United States Patent [19]

Man

[11] Patent Number: Plant 7,084

[45] Date of Patent: Dec. 26, 1989

[54] DISTINCT VARIETY OF BEGONIA PLANT NAMED MARIANDEL

[75] Inventor: Jan Man, Lisse, Netherlands

[73] Assignee: Oglevee Ltd., Connellsville, Pa.

[21] Appl. No.: 251,655

[22] Filed: Sep. 29, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Zeisenheim & Webb

[57] ABSTRACT

The new cultivar is generally characterized by its superior compact growth and flowering. The pink bloom contrast nicely with the rich green foliage. The inflorescence is long lasting with continuous bud protection.

1 Drawing Sheet

BACKGROUND OF THE NEW PLANT

The present invention comprises a new and distinct cultivar of *Begonia×hiemalis* known by the varietal name of Mariandel. The new cultivar is a sport of the cultivar Ilonka (U.S. Plant Pat. No. 6,203). The new cultivar is lighter in color than Ilonka with the tonality being more pink than peach. The new cultivar is shorter and has a more square-like form than Ilonka.

The new cultivar was discovered in August of 1984 at Limaplant b.v. in Lisse, Holland; was first asexually reproduced by cuttings at Limaplant b.v. in Lisse, Holland; and has been repeatedly asexually reproduced by cuttings for Oglevee Ltd. in Connellsville, Pa. It has been found to retain its distinctive characteristics through successive propagations.

The new cultivar is generally characterized by its superior compact growth and flowering. The pink bloom contrast nicely with the rich green foliage.

The new cultivar, when grown in a greenhouse in Connellsville, Pa., has a response time of 9 to 10 weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Ltd. in Connellsville, Pa. The plant history was taken on ten week plants blossomed under natural light in a greenhouse and grown under temperature conditions of 68° F. night and day. The plants were potted Feb. 2, 1988 in a peat-like mix and fertilized with a 5 ppm mixture of 20N-10P-20K. Color readings were taken indoors under 200 foot-candles of cool white fluorescent tubes. Color references are to The R.H.S. Colour Chart of The Royal Horticultural Society of London, unless noted differently.

Botanical classification: *Begonia×hiemalis.*

Flower:

*Fully expanded.*—5.5 to 6.0 cm. in diameter; side view: flattened oval in appearance.

*Borne.*—Compound dichasium (cyme).

*Stems.*—Strong, medium compact stem, average stem width 0.5 to 1.5 cm. in diameter; color yellow-green group 144C.

*Form.*—Semi-double to fully double. Each flower generally has 2 sepals and 3 to 6 petaloids (each group may vary ±1 structure).

*Permanence.*—Very long lasting bloom, average life span of 2 to 3 weeks.

Color:

*Tonality from a distance.*—Pink.

*Front of petals.*—Outer margin: red group 36B; remainder of petal is red group 38C.

*Reverse of petals.*—Characterized almost entirely by red group 39D.

*Base of petals.*—Red group 38C.

*Throat.*—None observed.

*Discoloration.*—None.

*Other comments.*—Older flower buds on outside edge red group 38A and lighter to yellow-green group 150D at very base of outside petal.

Petal:

*Texture.*—Crepe paper like (gentle crinkles).

*Appearance.*—Oval — clear pink color.

*Arrangement.*—Semi-double to fully double.

*Persistence.*—Very good. Flowers last long time up to 3 weeks and plant will continue to produce new buds.

*Fragrance.*—None observed.

Reproductive organs: All reproductive organs have modified into petaloids. Anthers, filament, pollen, style and ovaries could not be observed.

Plant:

*Form.*—Short compact, internodes 2 to 3 cm. apart; upright; good self-support strength, good basal branching.

*Growth.*—Very vigorous.

*Height from soil line.*—19 to 21 cm. in 10 weeks (no pinch, no cycocel).

*Spread.*—22 to 23 cm. in 10 weeks (no pinch, no cycocel.

Foliage:

*Size.*—Average length of 12 cm. and average width of 9 cm., on leaves 3 nodes up from base of stem.

*Quantity.*—Very abundant.

*Shape.*—Acute tip with irregularly lobed attachment; edge is slightly doubly serrate.

*Top side.*—Green group 139A.

*Underside.*—Green group 137C.

*Ribs and veins.*—Smooth on top side, raised on lower side, lower side veins only area on leaf where visible tricomes (hairs) appear.

*Rib and vein color.*—Top side: yellow-green group 145C; bottom: yellow-green group 146D.

*Margin.*—None.

*Stipules.*—None.

*Texture.*—Top: smooth, shiny and leathery; bottom: matt finish with raised veins.

I claim:

1. A new and distinct variety of Begonia characterized by superior compact growth, flowering, long lasting with continuous bud production and contrast of pink bloom on dark green foliage as shown and described herein.

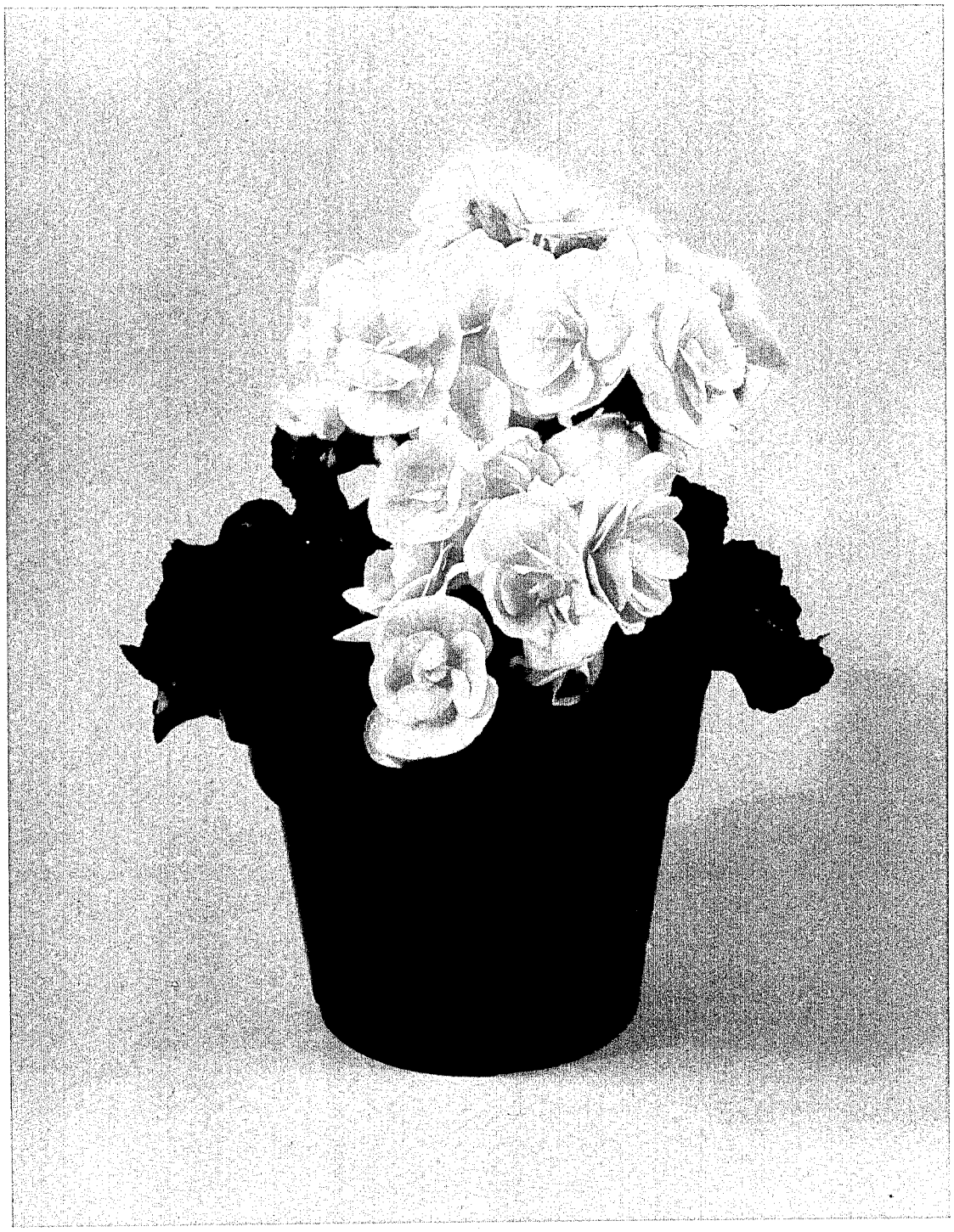

* * * * *